United States Patent [19]
Färber

[11] Patent Number: 6,110,160
[45] Date of Patent: *Aug. 29, 2000

[54] BLOOD EXTRACTION DEVICE HAVING A HOLDER AND A SHARPENED-END CANNULA

[75] Inventor: Horst Färber, Nümbrecht, Germany

[73] Assignee: Walter Sarstedt Gerate und Verbrauchsmaterial fur Medizin und Wissenschaft, Numbrecht, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/846,072

[22] Filed: Apr. 25, 1997

[30] Foreign Application Priority Data

Apr. 27, 1996 [DE] Germany .................. 196 17 000

[51] Int. Cl.⁷ .................................. A61B 19/00
[52] U.S. Cl. .................. 604/412; 604/240; 604/413; 600/576
[58] Field of Search .................... 600/576, 577; 604/232, 272, 411–414, 240

[56] References Cited

U.S. PATENT DOCUMENTS 4,846,808  7/1989  Haber et al. .................. 604/195

*Primary Examiner*—Corrine McDermott
*Attorney, Agent, or Firm*—Herbert Dubno

[57] ABSTRACT

A blood extraction device has a holder with a hollow needle cannula anchored therein. A rear end portion of this cannula is surrounded by a closed-end elastic hose like valve rubber tube with an air gap between the tube and the cannula. With a minimum of effort and cost a reliable anchorage of the valve rubber tube in the holder is obtained by pressing a clamping member within the holder against the exterior of the valve rubber tube and thereby plastically deforming this clamping member.

4 Claims, 1 Drawing Sheet

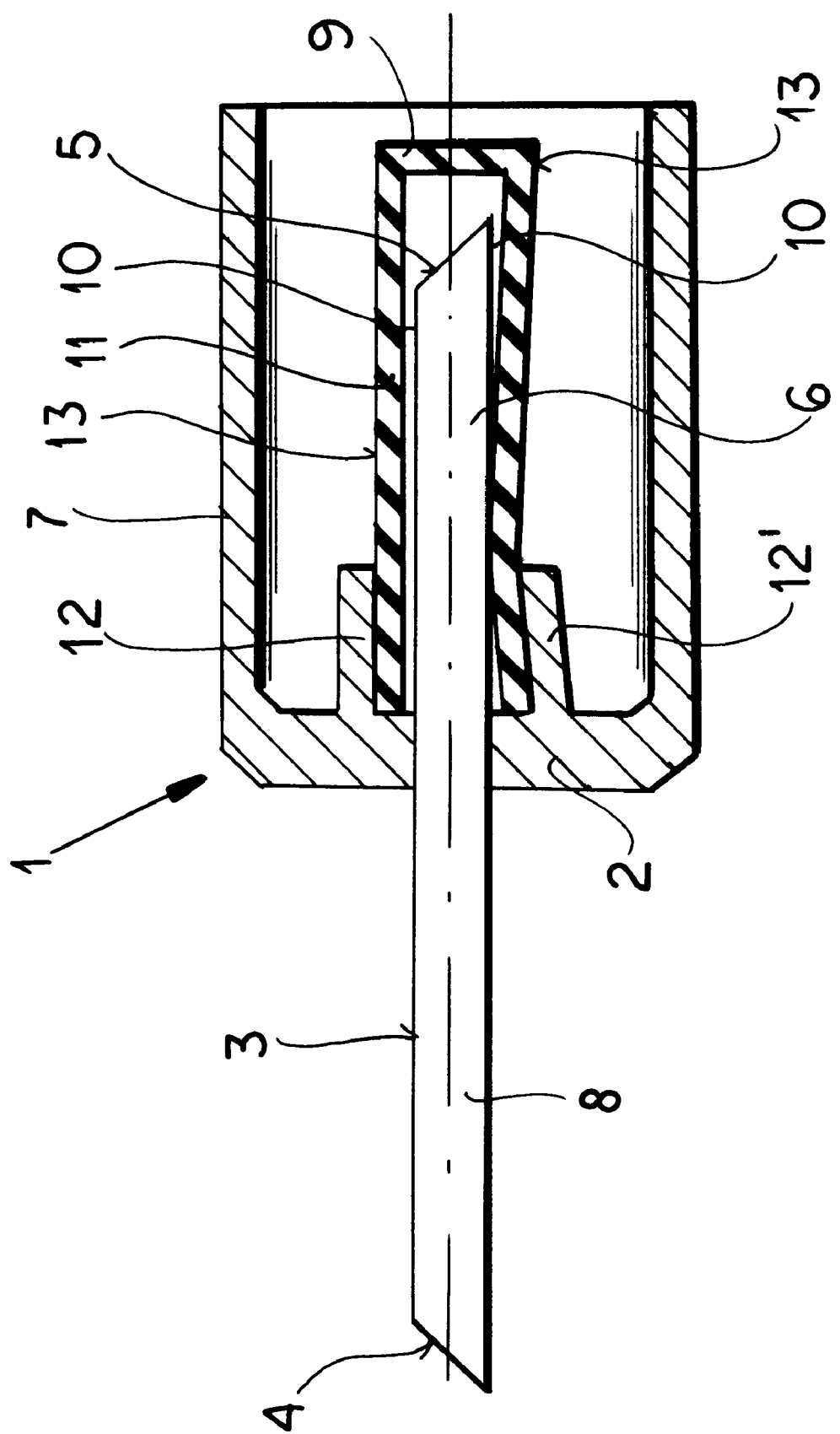

BLOOD EXTRACTION DEVICE HAVING A HOLDER AND A SHARPENED-END CANNULA

FIELD OF THE INVENTION

The present invention relates to a blood extraction device of the type which has a holder, a sharpened hollow needle cannula extending from this holder and, within the holder, a closed-end elastic hose-like valve rubber tube which surrounds the opposite end of the cannula and which is held within the holder.

BACKGROUND OF THE INVENTION

Blood extraction devices having a holder with a cannula and a closed end sleeve of valve rubber surrounding the end of the cannula within the chamber defined by the holder can be used for the extraction of blood from a blood vessel of a patient by inserting the sharpened end of the cannula outside the chamber into a blood vessel and inserting into the holder sampling tubes, for example, in succession, permitting the blood to flow through the cannula into the sampling tubes or allowing a syringe-type instrument to draw blood into a sampling vessel through the cannula.

Blood extraction devices utilizing these principles are known in a variety of configurations. For example, U.S. Pat. No. 3,585,984 discloses a blood extraction device with a holder from which a hollow needle cannula extends with a sharp-edged point. The cannula has, at its opposite end, a closed end elastic hose-like valve rubber tube or sleeve surrounding the cannula with an air gap between the cannula and the hose-like tube. The holder has a dome-like formation extending forwardly in which a thickened head or plug of the valve rubber tube projects. This head forms, in effect, a fixed portion of the valve-rubber sleeve which form-fittingly surrounds and engages the cannula and fictionally bears upon the latter internally and upon the holder externally.

A further blood extraction device is described in DE-C 18 12 742 which utilizes a tubular holder open at one end and which receives a hollow-needle double-pointed cannula whose rear end projects into a holder which also serves as a guide sleeve. While the rear end of the doubly-pointed cannula is surrounded by an elastic valve rubber, the front cannula end projects from the end wall of the holder forwardly and can be inserted into a vein of a patient. The blood passing through the cannula enters a sampling tube which is connected at the open end of the holder to the latter. By pushing together the holder and the sampling tube the rear end of the cannula pierces the bottom of the elastic valve rubber and the elastic stopper of the sampling tube so that the rear end of the cannula projects into the sampling tube. The elastic valve sleeve or rubber tube is compressed in an accordion-like manner. After the blood extraction has been completed and the sampling tube is withdrawn from the holder the hose-like valve rubber tube ultimately reassumes its sealing position closing the rear end of the cannula. The holder can be reduced to a disk, i.e. the guide sleeve can be omitted. In this case, the holder disk is connected with the dome of a cap of the blood sampling tube.

Still another configuration has been shown in DE-U 80 16 927 in which the double cannula is received in a cylindrical housing open at one side and provided with a one-piece external cone. On the external cone, a receiving cone of a holder provided with a sharpened cannula or hollow needle can be mounted so that after assembly the double cannula is formed. With this needle configuration, Luer-lock needles of the type commercially used with syringes and blood extraction or sampling tubes can be connected. Elastic rubber valve members can here closely surround the hollow needle of the holder or adapter. The adapter with its Luer cone can also be connected via special adapters or connectors to, for example, a blood-filled tube.

DE-A 29 03 167 discloses a safety cannula with multiple blood sampling in which an accordion like valve rubber tube surrounds a rear end of a double-pointed cannula with a radial air space or radial play. The valve rubber member here has over its entire length an inner diameter which is greater than the outer diameter of the cannula or hollow needle.

When the elastomeric valve member is too close to the needle, friction between the needle and the valve member is unavoidable (see DE-U 80 16 927) and as a result restoration of the elastomeric member from its accordion-like compacted position to its fully extending starting position may be delayed. In that case, upon changing of the blood sampling tube, the expression of blood drops from the cannula cannot be avoided. In general, therefore, it is desirable to avoid any delays in self-closure of the rear end of the cannula.

The frictional delay can be avoided by providing at the rear end of the needle a sufficient radial spacing of the flexible rubber tube from the needle (compare DE-A 29 03 167 and DE-C 18 12 742).

With these systems, the needle is not frictionally engaged by the hose like member but a problem arises in that the position of the hose like member in the holder or adapter cannot be reliably ensured.

The hose-like member in the blood extraction device in DE-C 18 12 742 is formed at its open end with an engagement shoulder which lies against an internal shoulder of the holder and is retained in this position solely by the friction between the surface of the shoulders. The flexible rubber valve sleeve of DE-A 29 03 167 is provided with an external shoulder at its open end which is seated in an annular groove of the end wall of the holder. Here as well the seating of the valve member tends to be loose or readily loosened upon use and problems can be encountered in the mounting of the hose-like valve member in the annular groove.

A variety of other fastening techniques have been used for the hose-like rubber valve member. For example, a form fitting connection is provided by drawing the valve rubber member over a cylindrical boss at a central region of the cannula in DE-A 37 40 269. In EP-A 0 619 096, the valve rubber hose is drawn over a ball-shaped edge bulge while, by contrast, WO-A 95/16395 teaches that the valve rubber tube can be pressed over a conical shoulder with undercuts and can there be cemented.

Finally, according to EP-A 0 678 279, the valve rubber member can be secured in a circumferential collar of circumferential edge within the holder and secured there by a plastic insert.

OBJECTS OF THE INVENTION

It is the principal object of the present invention to provide an improved blood extraction device in which the valve rubber tube can be retained reliably and securely and can be mounted with a minimum of cost in the holder or adapter.

Another object of the invention is to provide an improved blood extraction device which is free rom drawbacks of earlier devices for the purposes described.

SUMMARY OF THE INVENTION

These objects are attained, in accordance with the invention in that the valve rubber sleeve or tube, which is closed at one end, is engaged from the exterior by a fixed portion of the holder which can have a deformable clamping element which is deformed to clamp against the exterior of the tubular member.

As a consequence, the closed end valve rubber flexible tube is no longer loose or frictionally engaged within the holder and does not require adhesive bonding to secure it in place. The deformable clamping element suffices and the tube can neither be withdrawn from the cannula or roll out of the holder involuntarily. Furthermore, it cannot shift within the cannula. At the same time, the fact that the tube can retain its position relative to the double-pointed cannula at least at the rear end thereof, substantially over the entire length of the valve rubber flexible tube, ensures maintenance of a radial spacing around the cannula so that there is no friction delay in returning to the sealing position and the intrinsic elasticity of the tube can readily close off the rear end of the cannula when the sampling tubes are exchanged. A blood outflow from the rear end of the cannula is thus avoided.

The fabrication of the valve rubber tube requires no excessive concern with respect to contours and tolerances and no special sealing arrangement need be provided along the inner wall of the valve rubber tube.

The blood extraction device of the invention can thus comprise:

a holder having a chamber;

a hollow cannula fixed in the holder and having a sharpened pointed end externally of the chamber and adapted to pierce a blood vessel and another end extending into the chamber;

a closed-end flexible rubber valve tube surrounding the other end of the hollow cannula and defining an air-filled space between the valve tube and the other end of the cannula; and means on the holder engaging the valve tube from an outer side thereof and including a deformable member deformed inwardly into engagement with the valve tube to retain the valve tube in position in the chamber and on the housing.

BRIEF DESCRIPTION OF THE DRAWING

The above and other objects, features, and advantages of the invention will become more readily apparent from the following description, reference being made to the accompanying drawing, the sole FIGURE of which is a diagrammatic axial section through a holder of a blood extraction device according to the invention.

SPECIFIC DESCRIPTION

In the drawing I have shown a holder 1, open at one end and having an end wall 2 at the opposite end in which a double-pointed cannula 3 is anchored, e.g. by welding or adhesive bonding. A separate needle holder can thus be avoided. The double-pointed cannula 3 has sharpened cutting edges 4 and 5 at its front and rear ends. The rear portion 6 of the cannula 3 projects into the chamber surrounded by a guide sleeve 7 of the holder while the front portion 8 of the cannula 3 projects from the holder 1 and can be inserted into a vein of a patient.

For blood extraction, the sleeve 7, which forms a wall coaxial with the rear cannula portion, is pressed over a blood sampling tube, whereby the cutting edge 5 of the rear portion 6 of the cannula 3 pierces the bottom 9 of a rubber valve tube 11 surrounding the rear cannula portion and the elastic stopper or membrane of the blood sampling tube so that the cannula 3 will communicate with the interior of the blood sampling tube.

The open end of the rubber valve tube 11 is received in a tubular boss or sleeve 12 which forms a clamping element of which a portion 12', referred to here as the clamping member, is clenched against the rubber valve tube 11. The clamping element can also be formed by a separate peripherally closed ring, or a ring having segments which can be clenched against the rubber valve tube. The clamping member or clenched portion of the sleeve 12' engages the outer surface 13 of the rubber valve tube 11 and can plastically deform the rubber valve tube as has been shown at 12' in the drawing. The open end of the rubber valve tube 11 thus abuts the inner side of the end wall 2 in the annular space surrounded by the clamping element 12 and is securely held there by the deformation of one or more clamping members as has been described. An air gap is provided between the rubber valve tube 11 and the rear portion 6 substantially over the entire length thereof as represented at 10 so that, when the rubber valve tube 11 is compressed around the rear portion 6 as the cutting edge 5 is thrust into the sampling tube, there is no frictional retardation against expansion to the full length shown in the drawing in which the cutting edge 5 is closed from the atmosphere upon withdrawal of the sampling tube.

The deformation of the clamping member 12' or of individual clamping segments can be effected by a ram or stamper which can have a passage receiving the rear portion 6 of the cannula and the rubber valve tube tubular member 11. When the front portion of this passage is conically shaped and has a larger diameter than the sleeve-like formation 12 or the clamping elements surrounding the rubber valve tube 11, during the axial insertion of the stamp, a portion 12' will be pressed inwardly to clamp the rubber valve tube 11 non-releasably in the holder by plastic deformation as noted.

I claim:

1. A blood extraction device, comprising:

a holder having a chamber formed with an end wall;

a hollow cannula fixed in said end wall of said holder and having a sharpened pointed end externally of said chamber and adapted to pierce a blood vessel and another end extending into said chamber, said cannula having an outer surface of constant diameter between said ends;

a closed-end flexible rubber valve tube surrounding said other end of said hollow cannula and defining an air-filled space between said valve tube and said other end of said cannula; and means on said holder engaging said valve tube from an outer side thereof and including an axially inwardly extending deformable tubular member unitary with said end wall of said holder plastically and permanently deformed conically inwardly into radial engagement with said valve tube to press said valve tube against said surface of said cannula at least at a mouth of said tubular member to retain said valve tube in position in said chamber and on said holder.

2. The device defined in claim 1 wherein said holder has a wall coaxial with said other end of said cannula and delimiting said chamber.

3. The device defined in claim 2 wherein said tubular member is a boss surrounding said valve tube and inwardly clenched over only a portion of said boss against said surface.

4. The device defined in claim 1 wherein said cannula is a doubly pointed needle.

* * * * *